(12) United States Patent
Segall et al.

(10) Patent No.: US 7,867,611 B2
(45) Date of Patent: Jan. 11, 2011

(54) BIOMEDICAL SENSORS EMPLOYING HYDRO-INSENSITIVE ALTERNATING CURRENT RESPONSIVE COMPOSITES

(75) Inventors: Daniel P. Segall, Longmeadow, MA (US); Iris E. Hilton, Charlton, MA (US); Melissa E. Szymanski, Greenville, RI (US); John R. Pennace, Paxton, MA (US)

(73) Assignee: FLEXcon Company, Inc., Spencer, MA (US)

( * ) Notice: Subject to any disclaimer, the term of this patent is extended or adjusted under 35 U.S.C. 154(b) by 0 days.

(21) Appl. No.: 12/751,558

(22) Filed: Mar. 31, 2010

(65) Prior Publication Data

US 2010/0189952 A1    Jul. 29, 2010

Related U.S. Application Data

(63) Continuation of application No. 12/123,773, filed on May 20, 2008, now Pat. No. 7,713,447, which is a continuation of application No. 10/410,988, filed on Apr. 10, 2003, now Pat. No. 7,651,638.

(60) Provisional application No. 60/371,306, filed on Apr. 10, 2002.

(51) Int. Cl.
*A61B 5/04* (2006.01)
*A61B 5/0402* (2006.01)
*H01B 1/12* (2006.01)
*C09J 133/08* (2006.01)
*B32B 27/18* (2006.01)

(52) U.S. Cl. ............... 428/355 AC; 428/343; 428/355 R; 428/99; 600/391; 600/395; 600/509; 252/500; 252/519.3; 424/448; 424/484; 424/487

(58) Field of Classification Search ........... 428/355 AC, 428/355 R, 343, 99; 252/500, 519.3; 424/448, 424/484, 486, 487; 600/391, 395, 509
See application file for complete search history.

(56) References Cited

U.S. PATENT DOCUMENTS 3,911,906 A    10/1975    Reinhold, Jr.

(Continued)

FOREIGN PATENT DOCUMENTS

GB    2115431    9/1983

(Continued)

OTHER PUBLICATIONS

"A direct comparison of wet, dry, and insulating bioelectric recording electrodes," Searle et al. Physiological Measurement, Institute of Physics Publishing, Bristol, GB. vol. 21, No. 2. p. 271-283. May 1, 2000.

*Primary Examiner*—Stanley Silverman
*Assistant Examiner*—Kallambella Vijayakumar
(74) *Attorney, Agent, or Firm*—Gauthier & Connors LLP

(57) ABSTRACT

A biomedical sensor is disclosed that includes a conductive material for coupling to monitoring equipment, and a composite. The composite includes a polymeric material and a polar material that is substantially dispersed within the polymeric material. The composite has a first side that is coupled to the conductive material and has a second side that is positionable with respect to a subject to be monitored. The polar material exhibits molecular compatibility with the polymeric material such that the polar material neither blooms to a surface of the polymeric material nor crystallizes within the polymeric material.

20 Claims, 4 Drawing Sheets

U.S. PATENT DOCUMENTS

| | | |
|---|---|---|
| 4,008,721 A | 2/1977 | Burton |
| 4,074,000 A | 2/1978 | Hankee et al. |
| 4,293,665 A | 10/1981 | Zalucha et al. |
| 4,352,359 A | 10/1982 | Larimore et al. |
| 4,460,369 A | 7/1984 | Seymour |
| 4,798,773 A | 1/1989 | Yasukawa et al. |
| 4,848,353 A | 7/1989 | Engel |
| 5,120,325 A | 6/1992 | Dow, Jr. |
| 5,120,422 A | 6/1992 | Liu et al. |
| 5,143,071 A | 9/1992 | Keusch et al. |
| 5,338,490 A | 8/1994 | Dietz et al. |
| 5,362,420 A | 11/1994 | Itoh et al. |
| 5,388,026 A | 2/1995 | Kanbara et al. |
| 5,421,982 A | 6/1995 | Ikeda et al. |
| 5,645,062 A | 7/1997 | Anderson et al. |
| 5,800,685 A | 9/1998 | Perrault |
| 6,121,508 A | 9/2000 | Bischof et al. |
| 6,214,251 B1 | 4/2001 | Wu et al. |
| 6,232,366 B1 * | 5/2001 | Wang et al. .................. 523/111 |
| 6,327,487 B1 | 12/2001 | Stratbucker |
| 6,342,561 B1 | 1/2002 | Engel et al. |
| 6,576,712 B2 | 6/2003 | Feldstein et al. |
| 2002/0037977 A1 | 3/2002 | Feldstein et al. |
| 2004/0073104 A1 | 4/2004 | Brun del Re et al. |

FOREIGN PATENT DOCUMENTS

| | | |
|---|---|---|
| WO | WO9531491 | 11/1995 |
| WO | WO9724149 | 7/1997 |

* cited by examiner

BIOMEDICAL SENSORS EMPLOYING HYDRO-INSENSITIVE ALTERNATING CURRENT RESPONSIVE COMPOSITES

PRIORITY INFORMATION

The present application is a continuation of U.S. patent application Ser. No. 12/123,773 filed on May 20, 2008, now U.S. Pat. No. 7,713,447, which is a continuation of U.S. patent application Ser. No. 10/410,988 filed on Apr. 10, 2003, now U.S. Pat. No. 7,651,638, which claims priority to U.S. Provisional Patent Application Ser. No. 60/371,306 filed Apr. 10, 2002.

BACKGROUND OF THE INVENTION

The invention relates to polymeric materials that are used to conduct electrical signals, and relates in particular to conductive adhesives that are used with medical monitoring sensors that are placed directly on a patient, such as an electrocardiogram (EKG) sensor.

Electrically conductive pressure-sensitive adhesives for use in biomedical applications are disclosed, for example, in U.S. Pat. No. 4,848,353. Since such conductive materials typically depend on the presence of water, however, the material must be maintained in a sealed environment until being used. See also, U.S. Pat. No. 5,143,071, which discloses non-stringy adhesive gels for that are hydrophilic.

Such substances must be isolated from the environment prior to use (e.g., in sealed packages), and may function improperly if allowed to lose water from the conductive material. These limitations adversely affect both the cost of sensors that use such conductive adhesives as well as the amount of use that any particular sensor may enjoy.

There is a need therefore, for a material that may be used to conduct electricity yet is not susceptible to variations in the water vapor content of the environment in which it is used.

SUMMARY OF THE INVENTION

In accordance with an embodiment, the invention provides a biomedical sensor that includes a conductive material for coupling to monitoring equipment, and a composite. The composite includes a polymeric material and a polar material that is substantially dispersed within the polymeric material. The composite has a first side that is coupled to the conductive material and has a second side that is positionable with respect to a subject to be monitored. The polar material exhibits molecular compatibility with the polymeric material such that the polar material neither blooms to a surface of the polymeric material nor crystallizes within the polymeric material.

In accordance with another embodiment, the invention provides a biomedical sensor that includes a conductive material including an access node for coupling to monitoring equipment, and a non-ionically conductive composite. The non-ionically conductive composite includes a polymeric material and a polar material that is substantially dispersed within the polymeric material. The composite has a first side that is coupled to the conductive material, and the polar material exhibits molecular compatibility with the polymeric material such that the polar material neither blooms to a surface of the polymeric material nor crystallizes within the polymeric material. The non-ionically conductive composite provides a non-ionically conductive coupling between a subject and said conductive material.

In accordance with a further embodiment, the invention provides a biomedical sensor that includes a conductive material including an access node for coupling to monitoring equipment, and a clear adhesive composite. The clear adhesive composite includes a polymeric material and a polar material that is substantially dispersed within the polymeric material. The composite hays a first side that is coupled to the conductive material and has a second side that is positionable on a subject to be monitored. The polar material exhibits molecular compatibility with the polymeric material such that the polar material neither blooms to a surface of the polymeric material nor crystallizes within the polymeric material, and the polar material is responsive to an alternating electric field within the subject to provide a non-ionic coupling from the subject to the conductive material.

BRIEF DESCRIPTION OF THE DRAWING

The following description may be further understood with reference to the accompanying drawings in which.

The drawings are shown for illustrative purposes and are not to scale.

DETAILED DESCRIPTION OF THE INVENTION

Figure 1:
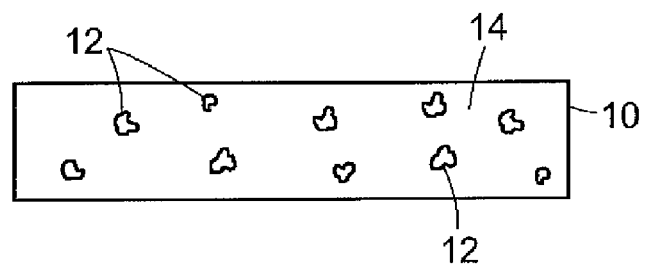
FIG. 1 shows an illustrative diagrammatic view of a composite in accordance with an embodiment of the invention.

It has been discovered that a polar material (such as an organo salt) may be dispersed within a polymeric material of sufficient concentration that the resulting composite may be responsive to the presence of an alternating current yet not be sensitive to water gain or loss from ambient temperature or humidity conditions. For example, as shown in FIG. 1, a composite 10 may include an organo salt 12 that is dispersed within a polymeric material 14. If the organo salt 12 has crystallized out of the polymeric material or has bloomed to the surface, then the salt is not compatible with that given polymer, thus the non-homogenous system will not respond to pick up the alternating current signal. If on the other hand, the salt becomes dissolved within the polymeric material (rendering the polymeric material clear), then the two materials are compatible, and a substantially homogenous mixture exists to form the desired alternating current responsive blend. When the salt is compatible with the polymer blend, it responds to the rise of an alternating current signal by orienting with the field then returning to a ground state with the collapse of the alternating current field. By responding to the presence of an electric field, therefore, the composite acts as a capacitor in coupling the signal (within a patient) to a sensor.

A suitable combination of polar material and polymeric material may be identified by the following procedure. First, a polar material is combined with the polymeric material in about five different concentrations (typically between about 5% to about 45% by weight). Then the adhesive-salt composite is drawn onto a release liner (of about 1.5 mil), and permitted to dry and cure. The surface of the composite is then inspected after a short period of time. If the salt has crystallized out or bloomed to the surface, then the combination of components is not compatible. If, on the other hand, the composite is clear, it is subject to the next level of compatibility testing. The samples should then be subjected an exposure test in which the samples are exposed to 100° F. with 95% relative humidity for 3 days. The samples are then again inspected to determine whether the polar material has migrated toward either surface. If there has been no migration of the polar material and the composite is clear, then the dielectric constant for the composite is determined and the composite is tested for use as a medical monitoring material. The dielectric constant, for example, may be at least 50 for signals at 200 Hz.

In accordance with an embodiment of the invention, the polymeric material may include an acrylic pressure sensitive adhesive such as the V-95 acrylic pressure sensitive adhesive sold by FLEXcon Corporation of Spencer, Mass. The polar material may include a quaternary ammonium organo salt such as the CHEMAX AS-3106 sold by Chemax Corporation of Beaumont, Tex. The percentage by weight of the polar material in the composite may for example, range from about 5% to about 65%, and preferably ranges from about 10% to about 35%.

Figure 2:
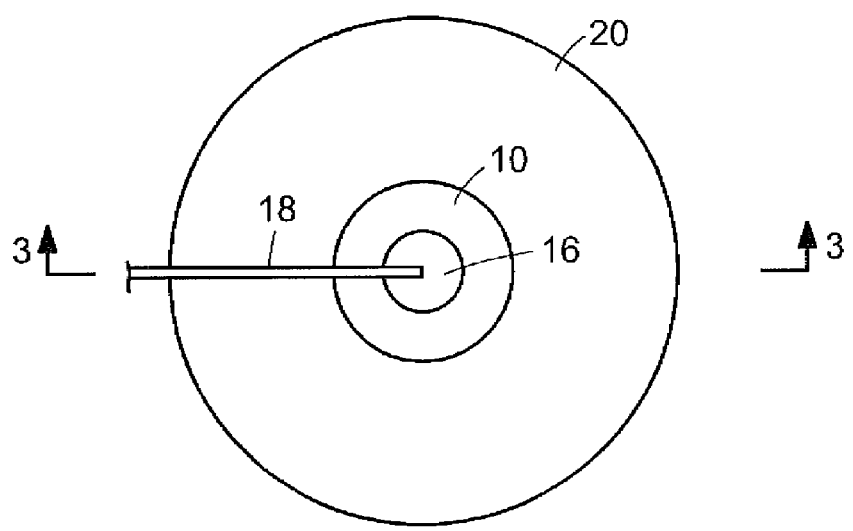
FIG. 2 shows an illustrative diagrammatic top view of a monitoring sensor using a composite in accordance with an embodiment of the invention.
Figure 3:
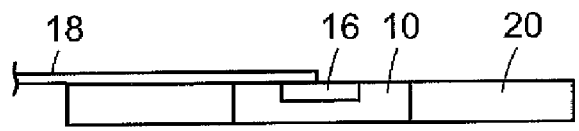
FIG. 3 shows an illustrative diagrammatic side view of the monitoring sensor shown in FIG. 2 taken along line 3-3 thereof.

As shown in FIGS. 2 and 3, the composite 10 may be used with medical diagnostic sensor pads in which a metallic contact element 16 is surrounded by the composite 10 and coupled to monitoring equipment via a conductor 18. The element 16 and composite 10 are positioned within an adhesive ployethylene foam carrier 20. In use, the sensor pad is placed on a patient's skin and internal alternating current signals (such as a heart rate) are received by the element 16 through the composite 10 and coupled to the monitoring equipment.

In further embodiments, the composite 10 may be used in a wide variety of other uses, including for example, other diagnostic sensors, as well as applications in fuel cell technology, battery technology, electro luminescence, or any other application in which an electrical current and/or signal is carried through an electrolyte that has at it's source a dependence on water. Composites of the invention are insensitive to the presence or absence of water vapor, and therefore, do not require high levels of maintenance of certain levels of water in packaging and during use. It has been discovered that the shortcomings of having an electrolyte dependent on the presence of water vapor are avoided by using for example organo-salts (quaternary ammonium salts, organo-sulfates, fluoroboarates, and other salt like materials having some organic functionality). The organic functionality facilitates the salt's organic compatibility with the polymeric material. Organic compatability may not be required when a polymer has compatibility with a purely inorganic salt, e.g., Cesium Iodide. An objective is to provide a polar material such as salt that is at least substantially uniformly dispersed throughout the polymeric material. The water insensitive composite may then respond to an ascending/collapsing electric field via a capacitive coupling. In view of the relatively high volume direct current resistance of this type of doped polymer, the sensitivity is towards alternating current (AC) rather than direct current (DC). The composite, therefore, may even be more effective at detecting an AC signal than carrying an electrical current.

Figure 4A:
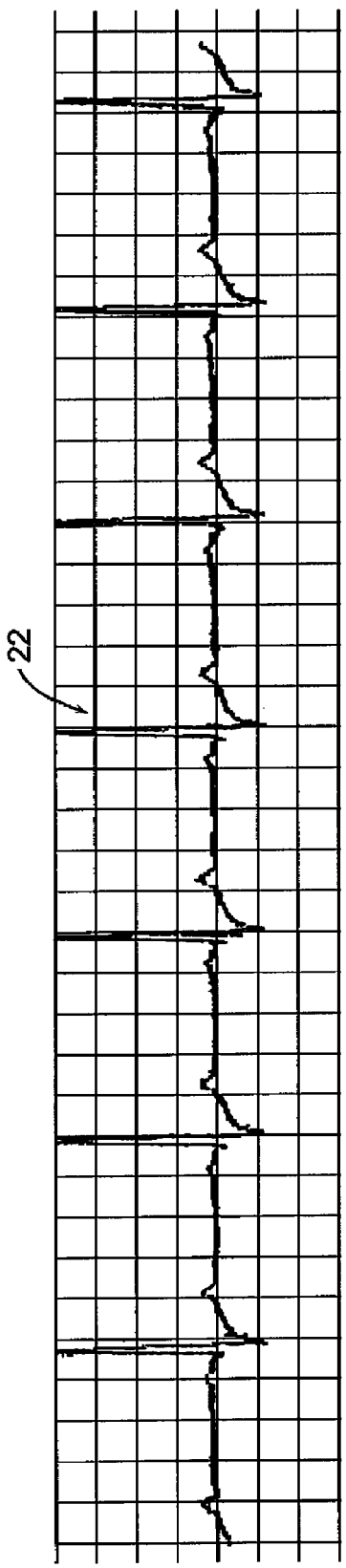
FIG. 4A shows an illustrative diagrammatic graphical representation of a patent signal being monitored by a conventional hydro-gel sensor.
Figure 4B:
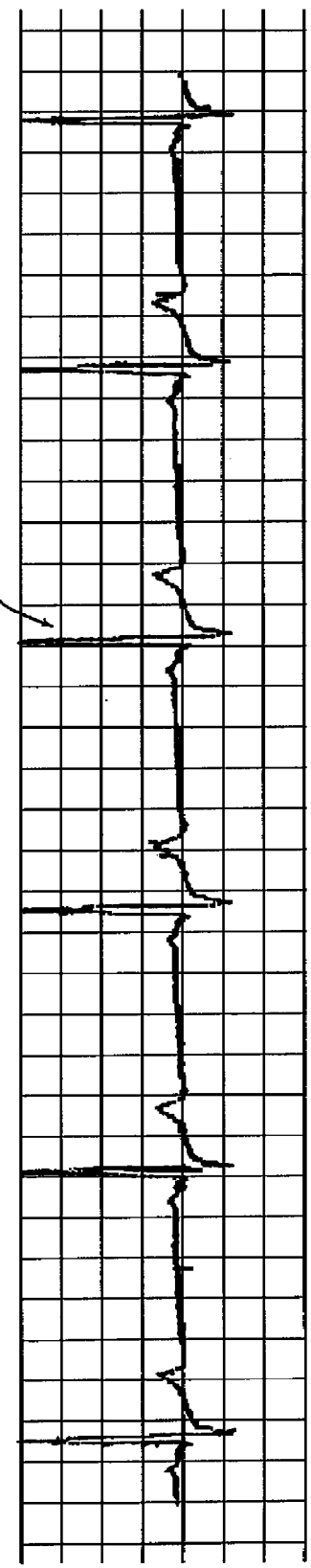
FIG. 4B show illustrative diagrammatic graphical representation of a patent signal being monitored by a sensor in accordance with an embodiment of the invention.
Figure 4C:
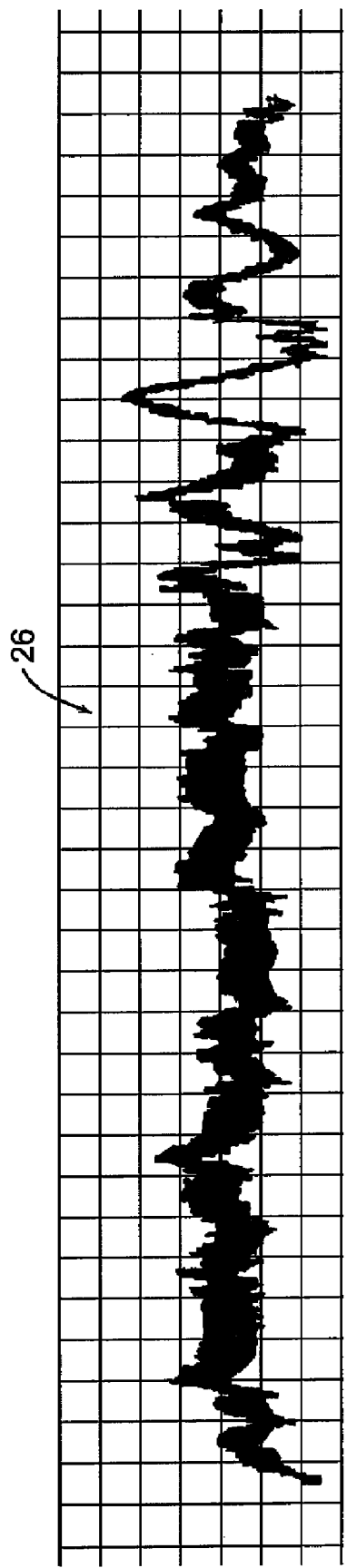
FIG. 4C shows an illustrative diagrammatic graphical representation of a patent signal being monitored by a sensor including a polymeric material but no polar material.

As discussed above with reference to FIGS. 2 and 3, composites of the invention may be used in place of electrolytic gels such as hydro-gels in cardiac monitoring pads. The monitoring pad with a composite of the invention described above was used to monitor a person's heart rate and the received signal was compared to signals received using a conventional hydro-gel electrolyte and using the polymeric material without doping with a polar material. As shown in FIG. 4B, the received signal using a composite of the invention (as shown at 24 in FIG. 4A) provided a nearly identical signal as the conventional hydro-gel electrolyte sensor (as shown at 22 in FIG. 4A). FIG. 4C shows that the received signal 26 using the polymeric material alone provided no discernable signal information.

Figure 5:
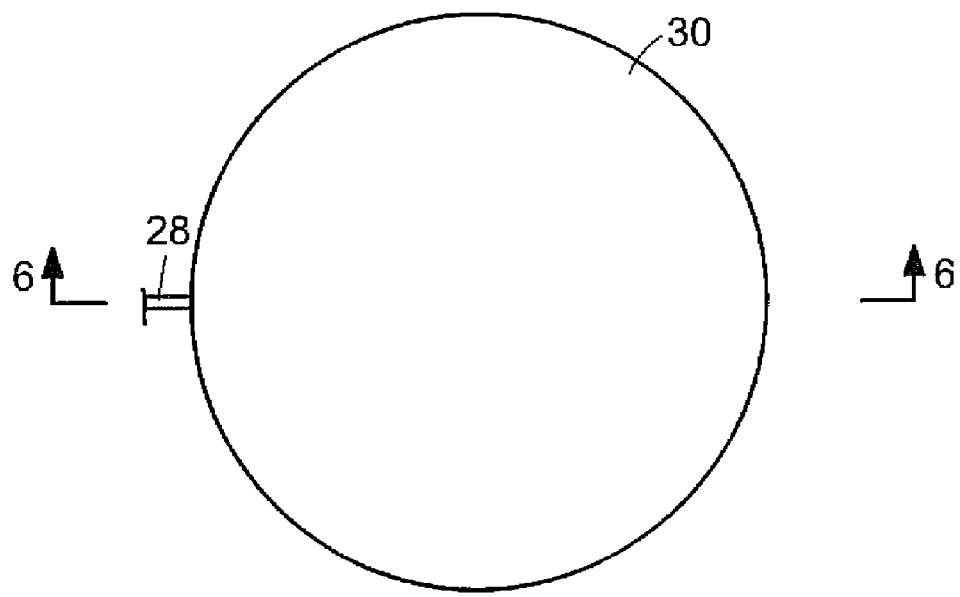
FIG. 5 shows an illustrative diagrammatic top view of a conductor pad using a composite in accordance with an embodiment of the invention.
Figure 6:
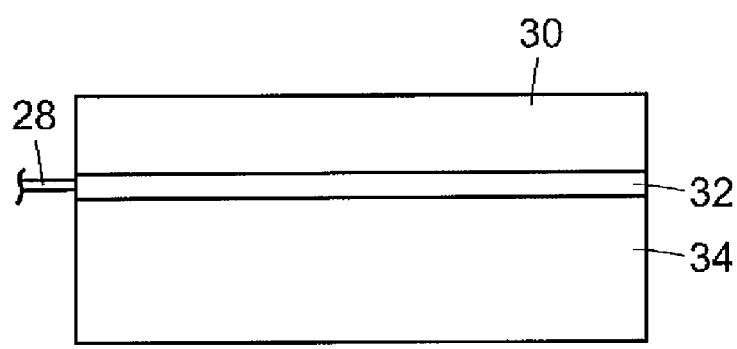
FIG. 6 shows an illustrative diagrammatic side view of the conductor pad shown in FIG. 5 taken along line 6-6 thereof.

Another variation of these monitoring pads is to provide a polymeric material that has sufficient adhesive qualities to be used itself as the adhesive without requiring the adhesive foam carrier 20. As shown in FIGS. 5 and 6, a conductor pad for use in medical applications may include a composite 30 of the invention that is sufficiently adhesive that no additional adhesive is required to maintain contact between a patient's skin and the pad. In this example, the pad used as a conductor to provide electrical signals via conductor 28 to a metallic conductor element 32. The alternating current field is then coupled to the patient via the composite 30 via the capacitive coupling characteristics of the composite. A supporting material 34 may also be used to provide structural integrity.

Composites of certain embodiments of the invention have also been tested at varying humidity and over extended periods of time and found to exhibit an insignificant amount of change in performance. Such composites have also been found to provide a recovery time after inducing an overloading current of within 5-10 seconds after the overloading condition was ceased. Although both the hydro-gel and composites of the invention act as a parallel capacitor/resistor, the hydro-gel has a DC resistance of about 500 ohms while a doped adhesive of the invention has a DC resistance of about 100K ohms or higher. The hydro-gel has a capacitance in both high (~10 kHz) and low (~200 Hz) frequency ranges in the microfarad range. The doped adhesive of an embodiment of the invention has a more pronounced capacitance that varies with frequency effect from about 230 Pico-farads at 10 kHz to about 1 microfarad at 200 Hz. The dielectric constant K must, therefore, be changing with frequency. In fact, at 10 kHz it is discovered that K is about 10, and at 200 Hz, K is about 10,000 or above. When the K is lower the resistance increases, which requires that the pad impedance and matching impedance of the monitoring equipment must be increased.

In other embodiments, the polymeric material may include various polymeric materials such as acrylic adhesives that may be distinguished by the relative composition of their monomers and by their molecular weights. For example, acrylic adhesives such as the DURO-TAK 80-1074 acrylic adhesive, the DURO-TAK 80-136A acrylic adhesive, or the DURO-TAK 87-2852 acrylic adhesive each of which sold by National Starch and Chemical Co. of Bridgewater, N.J. may be used as the polymeric material. In certain embodiments, the polar material may include organo-sulfonium, organic ester salts, organo-metallic materials, organo-borates, phosphates and phosfites etc. In particular, the polar material may include a quaternium 18 & isopropyl alcohol (such as the ARQUAD 2HT-75 product), dicocodimoium chloride & isopropyl alcohol (such as the ARQUAD 2C-75 product), stearyl octyldimonium methosulfate (such as the ARQUAD HTL8-MS product) each of which is sold by Akzo Nobel Surface Chemistry LLC of Chicago, Ill., or PEG-5 cocomonium chloride (such as the ETHOQUAD C/25 product sold by Brenntag N.V. of Deerlijk, Belgium). Suitable further specific combinations of polymeric materials and salts are provided in the following table using the above product names.

| Polar Material | Polymeric Material | Percent Polar Material by Weight |
| --- | --- | --- |
| ARQUAD 2HT-75 | 87-2852 | 20% |
| ARQUAD 2HT-75 | 87-2852 | 40% |
| ARQUAD 2C-75 | 87-2852 | 20% |
| ARQUAD 2C-75 | 87-2852 | 40% |
| ARQUAD 2C-75 | 80-136A | 20% |
| ARQUAD 2C-75 | 80-136A | 40% |
| ARQUAD HTL8-MS | 87-2852 | 20% |
| ARQUAD HTL8-MS | 87-2852 | 40% |
| ARQUAD HTL8-MS | 80-136A | 20% |
| ARQUAD HTL8-MS | 80-136A | 40% |
| ETHOQUAD C/25 | 87-2852 | 20% |
| ETHOQUAD C/25 | 87-2852 | 40% |
| ETHOQUAD C/25 | 80-136A | 20% |
| ETHOQUAD C/25 | 80-136A | 40% |

Composites of the invention may be employed in a wide variety of applications involving the coupling of alternating current electrical activity from one location to another, such as other applications involving the monitoring of electrical activity, or the active application of electrical activity, or even the grounding of undesired electrical activity in, for example, conductive housings.

Those skilled in the art will appreciate that numerous modifications and variations may be made to the above disclosed embodiments without departing from the spirit and scope of the invention.

The invention claimed is:

1. A biomedical sensor comprising a conductive material for coupling to monitoring equipment; and a composite including a polymeric material and a polar material that is substantially dispersed within the polymeric material, said composite having a first side that is coupled to said conductive material and having a second side that is positionable with respect to a subject to be monitored, wherein said polar material exhibits molecular compatibility with the polymeric material such that the polar material neither blooms to a surface of the polymeric material nor crystallizes within the polymeric material.

2. The biomedical sensor as claimed in claim 1, wherein said polymeric material is an adhesive.

3. The biomedical sensor as claimed in claim 1, wherein said polymeric material is an acrylic adhesive.

4. The biomedical sensor as claimed in claim 1, wherein said polymeric material is a pressure sensitive adhesive.

5. The biomedical sensor as claimed in claim 1, wherein said polar material is a salt.

6. The biomedical sensor as claimed in claim 1, wherein said polar material is an organic salt.

7. The biomedical sensor as claimed in claim 1, wherein said composite includes a concentration of said polar material within said polymeric material of between about 5% and about 65% based on weight.

8. The biomedical sensor as claimed in claim 1, wherein said composite includes a concentration of said polar material within said polymeric material of between about 10% and about 35% based on weight.

9. The biomedical sensor as claimed in claim 1, wherein said composite has a DC resistance of at least about 100 k Ohms.

10. The biomedical sensor as claimed in claim 1, wherein said composite has a dielectric constant that changes in the presence of and changes with an alternating electric field.

11. A biomedical sensor comprising a conductive material including an access node for coupling to monitoring equipment; and a non-ionically conductive composite that includes a polymeric material and a polar material that is substantially dispersed within the polymeric material, said composite having a first side that is coupled to said conductive material, wherein said polar material exhibits molecular compatibility with the polymeric material such that the polar material neither blooms to a surface of the polymeric material nor crystallizes within the polymeric material such that said non-ionically conductive composite provides a non-ionically conductive coupling between a subject and said conductive material.

12. The biomedical sensor as claimed in claim 11, wherein said polymeric material is an acrylic adhesive.

13. The biomedical sensor as claimed in claim 11, wherein said polymeric material is a pressure sensitive adhesive.

14. The biomedical sensor as claimed in claim 11, wherein said polar material is an organic salt.

15. The biomedical sensor as claimed in claim 11, wherein said composite includes a concentration of said polar material within said polymeric material of between about 5% and about 65% based on weight.

16. The biomedical sensor as claimed in claim 11, wherein said composite includes a concentration of said polar material within said polymeric material of between about 10% and about 35% based on weight.

17. The biomedical sensor as claimed in claim 11, wherein said composite has a DC resistance of at least about 100 k Ohms.

18. The biomedical sensor as claimed in claim 11, wherein said composite has a dielectric constant that changes in the presence of and changes with an alternating electric field.

19. A biomedical sensor comprising a conductive material including an access node for coupling to monitoring equipment; and a clear adhesive composite including a polymeric material and a polar material that is substantially dispersed within the polymeric material, said composite having a first side that is coupled to said conductive material and having a second side that is positionable on a subject to be monitored, wherein said polar material exhibits molecular compatibility with the polymeric material such that the polar material neither blooms to a surface of the polymeric material nor crystallizes within the polymeric material, and wherein said polar material is responsive to an alternating electric field within the subject to provide a non-ionic coupling from the subject to the conductive material.

20. The biomedical sensor as claimed in claim 19, wherein said composite has a dielectric constant that changes in the presence of and changes with the alternating electric field.

* * * * *